United States Patent [19]

Murashige et al.

[11] Patent Number: 4,639,339

[45] Date of Patent: Jan. 27, 1987

[54] SULFONATED POLYETHYLENEIMINE USEFUL AS BLOOD ANTICOAGULANT

[75] Inventors: Yoshio Murashige, Iwakuni; Akira Yanagase; Yasunori Kawachi, both of Ohtake; Junko Soga, Saiki, all of Japan

[73] Assignee: Mitsubishi Rayon Co., Ltd., Tokyo, Japan

[21] Appl. No.: 787,145

[22] Filed: Oct. 15, 1985

[30] Foreign Application Priority Data

Aug. 13, 1985 [JP] Japan ................................ 60-178069

[51] Int. Cl.$^4$ .......................................... C07C 143/86
[52] U.S. Cl. ................................................ 260/513.6
[58] Field of Search ...................................... 260/513.6

[56] References Cited

U.S. PATENT DOCUMENTS 2,201,762  5/1940  Cupery ............................. 260/513.6

Primary Examiner—Nicky Chan
Attorney, Agent, or Firm—Oblon, Fisher, Spivak, McClelland & Maier

[57] ABSTRACT

There is disclosed a blood anticoagulant consisting essentially of a sulfonated polyethyleneimine formed by sulfonating 1 mole % or more of the —NH— and —NH$_2$ groups present in a polyethyleneimine having a molecular weight of 300 or greater. This blood anticoagulant is suitable for preventing coagulation of blood collected for purpose of hematological examination.

2 Claims, No Drawings

SULFONATED POLYETHYLENEIMINE USEFUL AS BLOOD ANTICOAGULANT

BACKGROUND OF THE INVENTION

1. Field of the Invention

This invention relates to blood anticoagulants and, more particularly, to a blood anticoagulant suitable for preventing coagulation of blood collected for purposes of hematological examination.

2. Description of the Prior Art

With the progress of clinical medicine, hematological examination has recently come to play a very important role in the field of preventive medicine or in the judgement of therapeutic effects. Under these circumstances, the development of blood anticoagulants which can prevent coagulation of blood collected for purposes of hematological examination is being actively pursued.

Blood anticoagulants comprising heparin sodium are most widely known. For example, in medical treatments using an artifical kidney or a blood oxygenator, they are added to the blood and/or used for the treatment of equipment surfaces which are in contact with the blood.

Moreover, blood anticoagulants comprising a metallic salt of ethylenediaminetetraacetic acid are being used in certain morphological tests of blood.

These blood anticoagulants are also being used in coating the internal surfaces of hematocrit tubes for the determination of hematocrit which is an item of hematological examination, and as additives for the separation of blood plasma.

However, since heparin is obtained solely by extraction from animal organs, it cannot be produced as abundantly as synthetic products and its production cost is far higher. Moreover, it is difficult to obtain heparin preparations having an identical structure and identical properties by extraction from different types of organs.

On the other hand, blood anticoagulants comprising a metallic salt of ethylenediaminetetraacetic acid can be used in morphological tests of blood. However, they are disadvantageous in that they do not allow inorganic ion determinations which are among biochemical tests and they exert an adverse effect on enzyme tests. For these reasons, conventional blood tests have unavoidably involved complicated procedures, i.e., the selection of different blood anticoagulants according to the intended test item and the adoption of the serum separation method in which steps must be taken to separate serum from blood prior to measurement.

Accordingly, there is a demand for a blood anticoagulant which is inexpensive, has excellent anticoagulant properties, and exerts no adverse effect on a wide variety of blood tests. However, no blood anticoagulant meeting this demand has been developed as yet.

SUMMARY OF THE INVENTION

It is an object of the present invention to provide a blood anticoagulant which can be used without exerting any adverse effect on various types of blood tests.

It is another object of the present invention to provide a blood anticoagulant which exhibits stable anticoagulant properties and can be produced at low cost.

According to the present invention, there is provided a blood anticoagulant consisting essentially of a sulfonated polyethyleneimine formed by sulfonating 1 mole % or more of the —NH— and —NH$_2$ groups present in a polyethyleneimine having a molecular weight of 300 or greater.

DETAILED DESCRIPTION OF THE PREFERRED EMBODIMENTS

Polyethyleneimines are formed by ring-opening polymerization of ethyleneimine and, in many cases, have a branched structure containing primary, secondary and tertiary amino nitrogen atoms. The polyethyleneimine used in the present invention must have a molecular weight of 300 or greater. Molecular weights less than 300 are not suitable because the resulting product will have unsatisfactory anticoagulant properties. A polyethyleneimine which contain primary, secondary and tertiary amino nitrogen atoms in a ratio ranging from approximately 1:1:1 to approximately 1:3:1 may be suitably employed.

Such polyethyleneimines can be obtained by subjecting ethyleneimine to ring-opening polymerization in the presence of a catalyst selected from carbon dioxide, hydrochloric acid, hydrobromic acid, p-toluenesulfonic acid, aluminum chloride, boron trifluoride and the like.

In the blood anticoagulant of the present invention, 1 mole % or more of the —NH— and —NH$_2$ groups present in the aforesaid polyethyleneimine must be sulfonated. If the degree of sulfonation is less than 1 mole %, the sulfonated groups are not enough to exhibit satisfactory anticoagulant properties.

This sulfonated polyethyleneimine can be used as such, i.e., in sulfonic acid form. However, it is preferable to neutralize a part or all of the sulfonic groups with alkali metal, alkaline earth metal, ammonium or like ions. The reason for this is that, if it is used in sulfonic acid form and added to blood as an anticoagulant, the blood tends to undergo coagulation because of an increase in hydrogen ion concentration.

The method of sulfonating polyethyleneimines to form blood anticoagulants in accordance with the present invention will be described hereinbelow.

Typical examples of the method of sulfonating polyethyleneimines include sulfonation processes involving the reaction of a polyethyleneimine with chlorosulfonic acid, fuming sulfuric acid and hot concentrated sulfuric acid, respectively.

The sulfonation process using chlorosulfonic acid is carried out by dissolving a polyethyleneimine in a solvent such as methanol or the like and adding an appropriate amount of chlorosulfonic acid to effect reaction therebetween. Usable solvents include alcohols such as methanol, isopropanol, etc.; ketones such as acetone, methyl ethyl ketone, etc.; and halogenated hydrocarbons such as chloroform, carbon tetrachloride, dichloroethane, etc. In this case, the concentration of the polyethyleneimine dissolved in the solvent should be not lower than 0.5% by weight and not higher than 30% by weight. If the concentration is lower than 0.5% by weight, the amount of solvent used is so large that it will be difficult to recover the sulfonated product. On the other hand, if the concentration is higher than 30% by weight, it will be difficult to control the heat of reaction generated during the sulfonation reaction. Moreover, chlorosulfonic acid should preferably be used in an amount of not less than 10 parts by weight per 100 parts by weight of polyethyleneimine. If the amount is less than 10 parts by weight, the sulfonation reaction will not proceed to a full extent. In this sulfonation process, it is difficult to sulfonate both of the two primary amino hydrogen atoms of each amino group present in the polyethyleneimine, so that only one of them is usually sulfonated.

In the sulfonation process using fuming sulfuric acid, the sulfonation reaction can proceed under substantially the same conditions as described in connection with chlorosulfonic acid.

The sulfonation process using hot concentrated sulfuric acid is carried out by adding concentrated sulfuric acid having a concentration of 96 to 100% by weight directly to a polyethyleneimine and heating the resulting mixture. In this case, the degree of sulfonation is determined by the amount of sulfuric acid to be reacted with the polyethyleneimine, and the heating temperature. Specifically, the amount of sulfuric acid used should be not less than 50 parts by weight per 100 parts by weight of the polyethyleneimine. If the amount is less than 50 parts by weight, sulfonation with sulfuric acid will not proceed effectively. Concentrated sulfuric acid should preferably be added little by little to the polyethyleneimine, because local addition of a large amount of concentrated sulfuric acid may cause dehydration of the polyethyleneimine prior to sulfonation. After the addition of concentrated sulfuric acid, a reaction temperature equal to or higher than 100° C. and lower than 200° C. should suitably be maintained for a period of time ranging from 30 to 120 minutes. At higher temperatures, the sulfonation will be completed in a relatively short time, while at lower temperatures, the sulfonation will require a time of the order of 120 minutes. The degree of sulfonation of the polyethyleneimine can be confirmed by Fourier-transform infrared absorption spectroscopic analysis.

Since the sulfonated product of polyethyleneimine synthesized in the above-described manner contains unreacted chlorosulfonic acid, sulfuric acid and the like, such impurities should be removed according to a suitable purification procedure. For example, such impurities can be removed by dissolving the sulfonated product of polyethyleneimine in water, adding the resulting aqueous solution dropwise to a poor solvent miscible with water (for example, one selected from alcohols such as methanol, isopropanol, etc.; and ketones such as acetone, methyl ethyl ketone, etc.) to reprecipitate the product, separating the product so formed, and then drying it. In this purification procedure, the amount of water used to dissolve the sulfonated product of polyethyleneimine should preferably be as small as possible. Accordingly, it is preferable that the aqueous solution of the sulfonated product of polyethyleneimine which is added dropwise to a poor solvent for the purpose of reprecipitating the product has a concentration ranging from 10 to 80% by weight and more preferably from 30 to 60% by weight. If the concentration is lower than 10% by weight, only a small amount of the sulfonated product of polyethyleneimine will precipitate upon addition to a poor solvent, resulting in a reduced recovery. On the other hand, if the concentration is higher than 80% by weight, it will be difficult to prepare the aqueous solution of the sulfonated product.

The neutralization of the sulfonated product of polyethyleneimine may be carried out by preparing an aqueous solution of the sulfonated product and adding thereto a predetermined amount of an aqueous alkaline solution. The neutralizing agents which can be used for this purpose include sodium hydroxide, potassium hydroxide, magnesium hydroxide, barium hydroxide, ammonia, ammonium hydroxide and the like. The sulfonated product which has been neutralized with a metallic salt can also be purified by reprecipitation with a poor solvent selected from alcohols and the like.

In the blood anticoagulant of the present invention, the sulfonated product of polyethyleneimine may be used as such or in the form of an alkali metal, alkaline earth metal or ammonium salt or a mixture thereof. Moreover, the blood anticoagulant of the present invention may contain heparin salts, salts of oxalic acid, double salts of oxalic acid, salts of citric acid, and the like, so long as they are present in such low contents as to exert no influence on the results of blood tests.

The blood anticoagulants of the present invention is characterized in that it can be readily synthesized from polyethyleneimine which is a product obtained in chemical industry, it is inexpensive as compared with conventional blood anticoagulants, and it exhibits satisfactory anticoagulant properties without causing any change in the morphology of blood corpuscles.

The present invention is further illustrated by the following examples.

In these examples, the degree of sulfonation of the sulfonated polyethyleneimine was determined by Fourier-transform infrared absorption spectroscopic analysis.

EXAMPLE 1

5 g of polyethyleneimine having a weight average molecular weight of 10,000 and containing primary, secondary and tertiary amino nitrogen atoms in a ratio of 1:2:1 was dissolved in 50 ml of methanol. Then, 34 g of chlorosulfonic acid was added thereto little by little. After completion of the addition, the resulting mixture was heated to a reaction temperature of 60° C. with stirring and held at that temperature for 30 minutes to complete the reaction. During this reaction, the sulfonated product of polyethyleneimine precipitated as solvent-insoluble matter, which was separated by filtration through a glass filter. Then, 5 ml of water was added to the reaction product and the resulting aqueous solution was slowly added dropwise to 200 ml of stirred methanol to reprecipitate the reaction product. The reaction product so formed was separated and dried under reduced pressure to obtain 4.3 g of a powder. When the degree of sulfonation of this powder was determined, 27% of the —NH— and —NH$_2$ groups present in the polyethyleneimine were found to be sulfonated. A portion of this powder was taken and dissolved in water to prepare a 10 wt. % aqueous solution thereof. 5 $\mu$l, 2 $\mu$l, 1 $\mu$l and 0.5 $\mu$l aliquots of this 10 wt. % aqueous solution were separately placed in test tubes and about 1 ml of human fresh blood was added to each test tube. When these samples were visually examined 3 hours after the addition, none of them exhibited coagulation. Moreover, when these samples were observed under the light microscope to examine the morphology of blood corpuscles, no changes of red blood cells, white blood cells, platelets or the like were noted.

EXAMPLES 2 TO 9 AND COMPARATIVE EXAMPLE 1

The sulfonation of polyethyleneimines was carried out by varying the weight average molecular weight of polyethyleneimine used and the amount of chlorosulfonic acid added. In these polyethyleneimines, the primary, secondary and tertiary amino nitrogen atom ratios were approximately the same as the ratio of the polyethyleneimine used in Example 1. In each case, the starting polyethyleneimine was used in an amount of 5 g and the reaction temperature, reaction time, purification procedure and the like were the same as described in Example 1. The results thus obtained are shown in Table 1.

It can be seen from Comparative Example 1 that, when the weight average molecular weight of the starting polyethyleneimine was as low as 250, the sulfonation reaction did not proceed satisfactorily and the resulting product failed to act as an effective blood anticoagulant.

ondary and tertiary amino nitrogen atoms in a ratio of 1:2:1 was taken, and 5 g of concentrated sulfuric acid having a purity of 98% by weight was slowly added dropwise thereto and mixed therewith. Then, the resulting sulfuric acid solution was heated to 120° C. and held at that temperature for 90 minutes. During this period, the sulfuric acid solution was continuously stirred so as to prevent it from being locally heated. After the addition and dissolution of 10 c.c. of water, the reaction

TABLE 1

|  |  | Weight average molecular weight of starting polyethyleneimine | Amount of chlorosulfonic acid (g) | Degree of sulfonation (%) | Yield (g) | Anticoagulant properties* | Morphology of blood corpuscles |
|---|---|---|---|---|---|---|---|
| Example | 2 | 10,000 | 3.4 | 1.8 | 4.2 | | |
|  | 3 | " | 8.5 | 6 | 4.6 | | |
|  | 4 | " | 17 | 13 | 4.5 | | |
|  | 5 | " | 31 | 34 | 4.7 | | |
|  | 6 | " | 85 | 67 | 4.6 | | |
|  | 7 | 1,800 | 25.5 | 16 | 4.4 | | |
|  | 8 | 1,000 | 25.5 | 18 | 4.1 | | |
|  | 9 | 600 | 25.5 | 15 | 3.6 | | |
| Comparative Example | 1 | 250 | 25.5 | 0.3 | 3.0 | X | |

*Anticoagulant properties were evaluated according to the following procedure:
(1) 100 μl of a 1 wt. % aqueous solution of the sulfonated product of polyethyleneimine was placed in a test tube and 1.0 ml of fresh blood was added thereto. Then, the test tube was allowed to stand.
(2) The blood was visually examined for coagulation at intervals of 30 minutes and this examination was continued for 5 hours. The case in which no coagulation was noted is represented by , and the case in which partial coagulation was noted is represented by X.
(3) Where no coagulation was noted, the blood was observed under the light microscope to examine the occurrence of morphological changes of platelets and blood cells. means no changes were observed.

EXAMPLE 10

1 g of the sulfonated product of polyethyleneimine synthesized in Example 1 was taken and dissolved in 9 c.c. of water to prepare a 10 wt. % aqueous solution of the reaction product. This aqueous solution was neutralized by adding 2.8 ml of a 4N aqueous solution of sodium hydroxide, and then slowly added dropwise to 400 ml of methanol to reprecipitate the reaction product. The reaction product so formed was separated and dried under reduced pressure to obtain 0.78 g of a powder.

This powder was tested for anticoagulant properties in the same manner as described in Example 2. Specifically, its anticoagulant properties were evaluated by placing 100 μl of a 1.0 wt. % aqueous solution of the powder in a test tube and adding thereto about 1.0 ml of human blood. No coagulation of the blood was noted even after 5 hours.

When this sample was observed under the microscope, no agglutination of red blood cells, white blood cells or platelets was noted.

EXAMPLE 11

5 g of polyethyleneimine having a weight average molecular weight of 1,800 and containing primary, secmixture was added dropwise to 500 ml of methanol to reprecipitate the reaction product. Any residual sulfuric acid was removed by washing with methanol. The separated reaction product was dried under reduced pressure to obtain 3.6 g of a crystalline powder. The degree of sulfonation of this reaction product was determined to be 12%. Its anticoagulant properties were evaluated by preparing a 1.0 wt. % aqueous solution of the powder, placing 100 μl and 50 μl aliquots of the solution in test tubes, and adding about 1.0 ml of human blood to each test tube. Thus, no coagulation of the blood was noted even 5 hours after its addition. When these samples were observed under the microscope, no abnormalities of red blood cells, white blood cells or platelets were noted.

What is claimed is:

1. A sulfonated polyethyleneimine formed by sulfonating 1 mole % or more of the —NH— and —NH$_2$ groups present in a polyethyleneimine having a molecular weight of 300 or greater.

2. The sulfonated polyethyleneimine of claim 1 wherein at least a part of the sulfonic groups present in the sulfonated polyethyleneimine has been neutralized with alkali metal, alkaline earth metal or ammonium ions.

* * * * *